(12) United States Patent  
Shapiro et al.

(10) Patent No.: US 11,890,226 B2  
(45) Date of Patent: Feb. 6, 2024

(54) DEVICE AND METHODS FOR DIRECTING AGENTS INTO AN EYE

(71) Applicant: University of Maryland, College Park, College Park, MD (US)

(72) Inventors: Benjamin Shapiro, Washington, DC (US); Aleksandar Nacev, Bethesda, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/316,482

(22) Filed: Jun. 26, 2014

(65) Prior Publication Data

US 2015/0374543 A1    Dec. 31, 2015  
US 2019/0282400 A9    Sep. 19, 2019

Related U.S. Application Data

(63) Continuation-in-part of application No. 13/684,521, filed on Nov. 24, 2012, now Pat. No. 10,688,292, which is a continuation of application No. 12/712,182, filed on Feb. 24, 2010, now Pat. No. 8,316,862.

(60) Provisional application No. 61/839,736, filed on Jun. 26, 2013, provisional application No. 61/155,223, filed on Feb. 25, 2009.

(51) Int. Cl.  
*A61F 9/00* (2006.01)  
*A61N 2/06* (2006.01)  
*A61N 2/00* (2006.01)  
*A61M 37/00* (2006.01)

(52) U.S. Cl.  
CPC .......... *A61F 9/0026* (2013.01); *A61F 9/0017* (2013.01); *A61M 37/00* (2013.01); *A61N 2/002* (2013.01); *A61N 2/06* (2013.01); *A61M 2037/0007* (2013.01)

(58) Field of Classification Search  
CPC ..... A61F 9/0026; A61F 9/0017; A61N 2/002; A61N 2/06  
USPC ................................ 600/9–15; 128/897–899  
See application file for complete search history.

(56) References Cited

U.S. PATENT DOCUMENTS

| | | |
|---|---|---|
| 4,869,247 A | 9/1989 | Howard, III et al. |
| 6,015,377 A | 1/2000 | Brown et al. |
| 6,241,671 B1 | 6/2001 | Ritter et al. |
| 6,475,223 B1 | 11/2002 | Werp et al. |
| 6,562,019 B1 | 5/2003 | Sell |

(Continued)

FOREIGN PATENT DOCUMENTS

| | | |
|---|---|---|
| CA | 2753753 A1 | 9/2010 |
| EP | 2391725 A1 | 12/2011 |

(Continued)

OTHER PUBLICATIONS

Forbes, et al., An Approach to Targeted Drug Delivery Based on Uniform Magnetic Fields, 3372-3377, IEEE Transactions on Magnetics, vol. 39, No. 5 (Sep. 2003).

(Continued)

*Primary Examiner* — Sunita Reddy  
(74) *Attorney, Agent, or Firm* — Wilson Sonsini Goodrich & Rosati (57) ABSTRACT

A method, system, and device for magnetically pushing agents into an eye. The agents are magnetic or magnetizable or magnetically responsive.

10 Claims, 7 Drawing Sheets

(56) References Cited

U.S. PATENT DOCUMENTS

| | | | |
|---|---|---|---|
| 6,617,153 | B2 | 9/2003 | Kuehnle et al. |
| 6,689,044 | B2 | 2/2004 | Kirschabum |
| 6,776,165 | B2 | 8/2004 | Jin |
| 6,842,324 | B2 | 1/2005 | Eyssa |
| 6,975,197 | B2 | 12/2005 | Creighton, IV |
| 7,182,089 | B2 | 2/2007 | Ries |
| 7,305,263 | B2 | 2/2007 | Creighton, IV |
| 7,189,198 | B2 | 3/2007 | Harburn et al. |
| 7,344,491 | B1* | 3/2008 | Seeney ............... H04R 25/606 600/25 |
| 7,523,608 | B2 | 4/2009 | Shapiro et al. |
| 7,651,598 | B2 | 1/2010 | Shapiro et al. |
| 8,110,083 | B1 | 2/2012 | Shapiro et al. |
| 8,316,862 | B2 | 11/2012 | Shapiro et al. |
| 8,579,787 | B2 | 11/2013 | Shapiro et al. |
| 8,888,674 | B2 | 11/2014 | Shapiro et al. |
| 9,108,035 | B2 | 8/2015 | Shapiro et al. |
| 9,622,809 | B2 | 4/2017 | Weinberg |
| 10,576,295 | B2 | 3/2020 | Shapiro et al. |
| 10,688,292 | B2 | 6/2020 | Shapiro et al. |
| 2002/0127722 | A1 | 9/2002 | Kuehnle et al. |
| 2002/0133115 | A1 | 9/2002 | Gordon et al. |
| 2003/0120202 | A1 | 6/2003 | Gordon |
| 2004/0086572 | A1* | 5/2004 | Dailey ............... A61K 9/0043 424/489 |
| 2004/0096511 | A1* | 5/2004 | Harburn ............ A61K 9/0009 424/489 |
| 2004/0100618 | A1* | 5/2004 | Barker ............... A61B 3/0083 351/206 |
| 2004/0135971 | A1* | 7/2004 | Ulbers ............... A61B 3/135 351/221 |
| 2005/0192478 | A1 | 9/2005 | Williams et al. |
| 2005/0195360 | A1* | 9/2005 | Akita ................. A61B 3/135 351/212 |
| 2005/0203333 | A1* | 9/2005 | Dailey ............... A61F 2/147 600/37 |
| 2005/0228075 | A1 | 10/2005 | Gogos et al. |
| 2005/0271732 | A1* | 12/2005 | Seeney .............. A61K 9/0009 424/489 |
| 2006/0142632 | A1* | 6/2006 | Meretei ............. A61B 17/3207 600/12 |
| 2006/0165805 | A1* | 7/2006 | Steinhoff .......... A61K 47/48046 424/489 |
| 2006/0228421 | A1* | 10/2006 | Seeney ............... A61N 2/12 977/906 |
| 2007/0016006 | A1 | 1/2007 | Shachar |
| 2007/0299550 | A1 | 12/2007 | Nishijima et al. |
| 2008/0199400 | A1* | 8/2008 | Dyer ................... A61K 9/0046 424/9.1 |
| 2009/0030261 | A1* | 1/2009 | Whitmore .......... A61F 9/00 600/12 |
| 2009/0062828 | A1* | 3/2009 | Marr ................. A61B 17/00234 606/159 |
| 2009/0093669 | A1* | 4/2009 | Farone ............... A61K 31/16 514/447 |
| 2009/0226521 | A1* | 9/2009 | Smyth ............... A61K 47/6921 424/484 |
| 2009/0287036 | A1 | 11/2009 | Shapiro et al. |
| 2010/0212676 | A1* | 8/2010 | Shapiro .............. A61M 37/00 128/899 |
| 2011/0054237 | A1 | 3/2011 | Shapiro et al. |
| 2011/0060320 | A1 | 3/2011 | Aharon-Attar |
| 2011/0144411 | A1* | 6/2011 | Sandhu .............. A61K 9/5094 600/13 |
| 2011/0287951 | A1 | 11/2011 | Emmert-Buck et al. |
| 2012/0092105 | A1 | 4/2012 | Weinberg et al. |
| 2014/0336616 | A1* | 11/2014 | Edwards ............ A61N 2/002 604/173 |
| 2015/0238357 | A1* | 8/2015 | Goldberg ........... A61N 2/00 600/431 |
| 2015/0305929 | A1* | 10/2015 | Goldberg ........... G02B 1/043 604/521 |
| 2016/0101043 | A1* | 4/2016 | Mousavikhamene ....... A61F 9/0017 600/12 |

FOREIGN PATENT DOCUMENTS

| | | |
|---|---|---|
| EP | 2401024 A2 | 1/2012 |
| WO | WO-2007058966 A1 | 5/2007 |
| WO | WO-2009000478 A1 | 12/2008 |
| WO | WO-2009076465 A1 | 6/2009 |
| WO | 2009086071 | 7/2009 |
| WO | WO-2010088517 A1 | 8/2010 |
| WO | WO-2010099552 A2 | 9/2010 |
| WO | WO-2014210362 A1 | 12/2014 |

OTHER PUBLICATIONS

Goodwin et al., Targeting and retention of magnetic targeted carriers (MTCs) enhancing intra-arterial chemotherapy, Journal of Magnetism and Magnetic Materials, 194, 132-139 (1999).

Hayden and Hafeli, Magnetic Bandages for targeted delivery of therapeutic agents, Institute of Physics Publishing, Matter 18, S2877-S22891 (2006).

Kopke, et al., Magnetic Nanoparticles: Inner Ear Targeted Molecule Delivery and Middle Ear Implant, Audiol Neurotol, 11:123-133 (2006).

Yesin, et al., Analysis and Design of Wireless Magnetically Guided Microrobots in Body Fluid, Proceeding of the 2004 IEEE International Conference on Robotics and Automation, New Orleans, LA (Apr. 2004).

Lubbe et al., Clinical Experiences with Magnetic Drug Targeting: A Phase I Study with 4'-Epidoxorubicin in 14 Patients with Advanced Solid Tumors, Cancer Research, 56, 4689-4693 (1996).

Meeker, et al., Optimal Realization of Arbitrary Forces in Magentic Stereotaxis System, IEEE Transactions on Magnetics, vol. 32, No. 2 (Mar. 1996).

Senyei, et al., Magnetic Guidance of Drugcarrrying Microspheres, Journal of Applied Physics, 49, 3578 (1978).

Tamaz, et al., Real-Time MRI-Based Control of Ferromagnetic Core for Endovascular Navigation, IEEE Transactions on Magnetics, vol. 55, No. 7 (Jul. 2008).

Xu, et al., Site-directed Research of Magnetic Nanoparticles in Magnetic Drug Targeting, Journal of Magnetism and Magnetic Materials, 293, 514-519 (2005).

Yesin, et al., Modeling and Control of Untethered Biomicrorobots in a Fluidic Environment Using Fields, Institute of Robotics and Intelligent SYstems, 25:527 (2006).

International Search Report and Written Opinion dated Sep. 4, 2014.
ESR14817471 Extended European Search Report dated Feb. 2, 2017.

* cited by examiner

Animal Experiments

DEVICE AND METHODS FOR DIRECTING AGENTS INTO AN EYE

BACKGROUND

This disclosure relates generally to the delivery of therapeutic agents to an eye of a mammal. More specifically, this disclosure relates to the delivery of therapeutics agents, pharmaceutical agents, molecular agents, nucleotides, proteins, or cells (e.g., stem cells) into the eye and their use in allowing such therapeutic agents to be administered into the eye.

SUMMARY

This disclosure includes a method for treating a patient or animal that includes providing a delivery device capable of generating a magnetic field, placing the device proximal to a subject's eye, and pushing the therapeutic agent into the subject's eye via the device, wherein the therapeutic agent is pushed to a treatment site.

Additional features of the disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION

Specific embodiments provide methods, devices and systems for directing an active or therapeutic agent to and into the eye. One exemplary embodiment is a device 10 for magnetically-assisted delivery of an active agent schematically shown in FIG. 1. One operative principle for magnetically directing the agents (or therapeutic agents) associated with magnetic particles (e.g. with $Fe_3O_4$ cores), which includes magnetizable and magnetically responsive nanoparticles, involves an arrangement of magnets 12 or magnetizable elements 12, which can have a North (N) and a South (S) pole, to direct magnetic-particle formulations or agents 20 from a fluid/gel solution applied away from the targeted site (e.g. on the surface near the targeted site, or in the vicinity of targeted tissues) to the targeted site. Using this principle, the device with its plurality of magnets or magnetic elements can, for example, direct the agent ((magnetic, magnitizable or magnetic responsive (nano or micro sized)) from the fluid/gel solution/saline to the target site.

Figure 1:
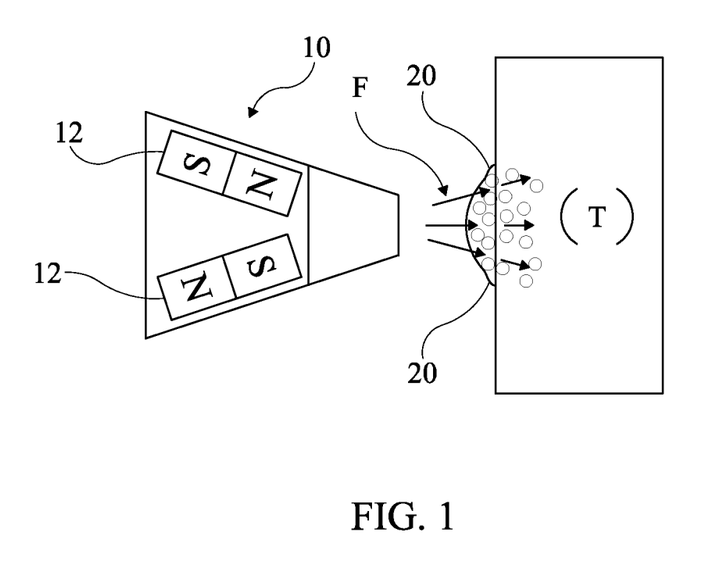
FIG. 1 shows one exemplary embodiment of a device for magnetically-assisted delivery of an active agent.

In one specific embodiment, active agents, e.g. particles associated with a therapeutic agent, can be applied away from a target site (e.g., away from the vitreous or the retina), and the device 10 can "push" or apply a force (F) on the therapeutic agents to the target site (T). The therapeutic agents can be pushed into and through ocular compartments (into for example, the lens, the vitreous humor, the optic nerve, and to the retina). The device 10 can be used to position or concentrate agents to targets within the eye, e.g. to the macula. For example, using device 10 according to certain methods, magnetic particles can be selectively positioned within the eye or concentrated at a higher concentration at a desired location.

In another specific embodiment, a method for treating a subject, patient or animal comprises (a) placing the device proximal to the patient's eye or animal's eye, and (b) magnetically pushing an active agent into and/or within the eye. Alternatively, the active agent may be placed within the eye and pushed to a desired section or location of the eye. Such methods can be atraumatic or reduce trauma, can deliver a therapeutically effective amount or a concentrated dose of the agent(s) to the eye. In some examples, the method can effectively deliver treatment to ocular diseases such as, by example, macular degeneration, retinitis pigmentosa, diabetic maculopathy, retinal vein occlusion, endophthalmitis, or the onset of congenital blindness by local/topical treatment.

Figure 2:
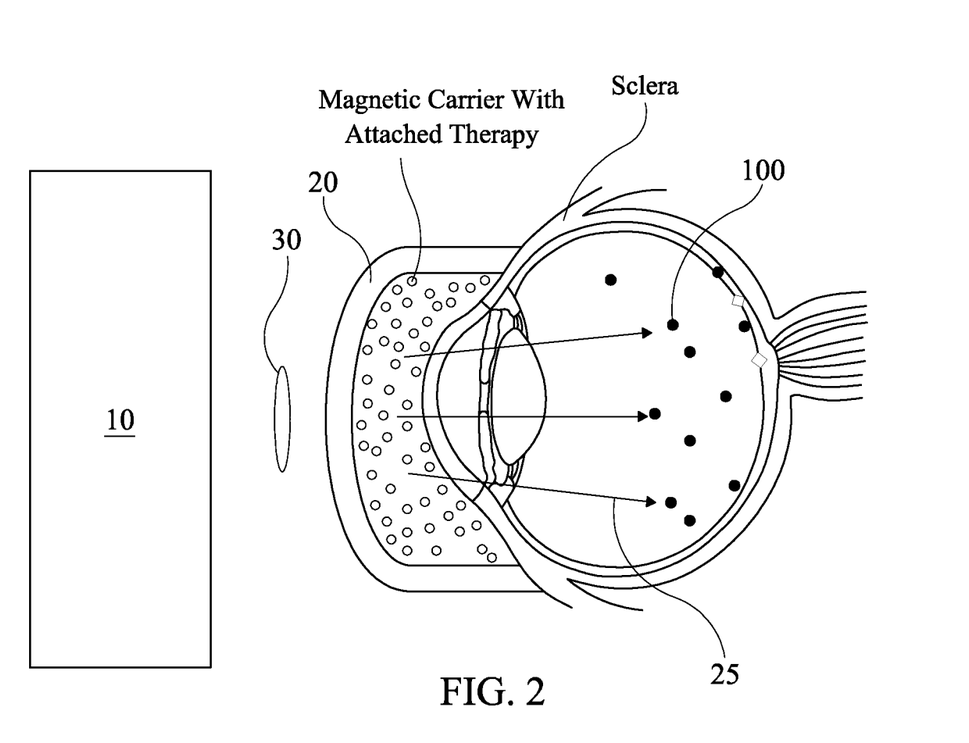
FIG. 2 shows one illustrative example of a magnetic device capable of directing or applying a force on a magnetic or magnetizable agent into an eye.
Figure 3A:
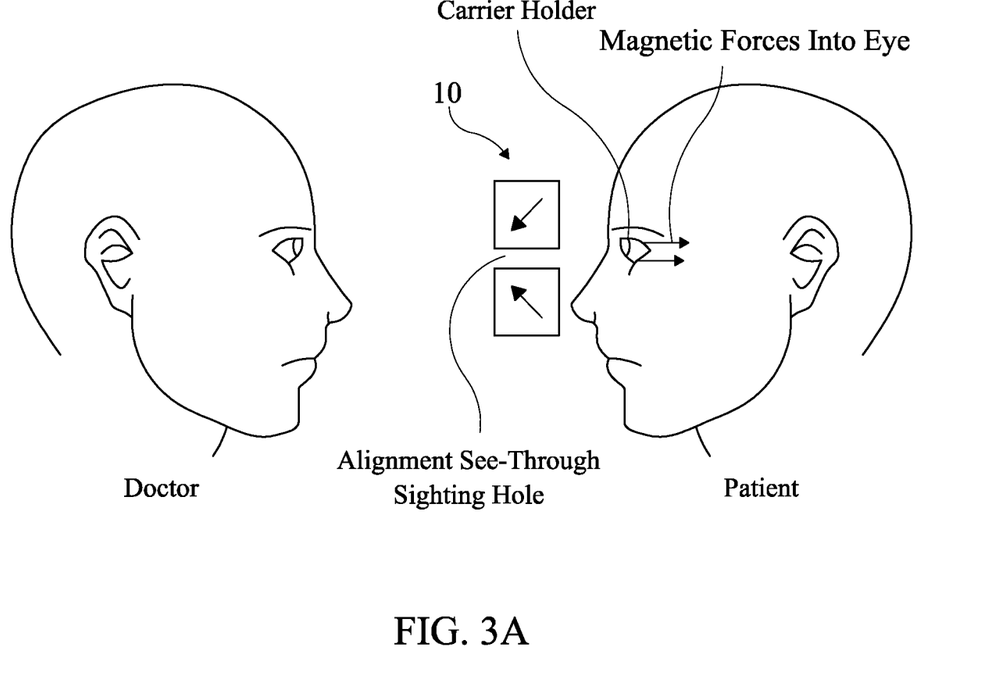
FIG. 3A illustrates one aspect of a method for aligning the device with a subject.
Figure 3B:
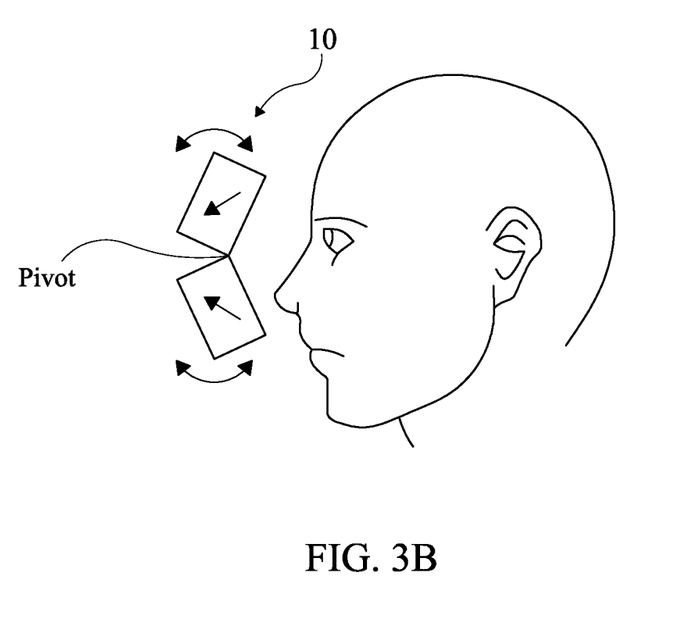
FIG. 3B illustrates another aspect of a method for aligning the device with a subject.
Figure 3C:
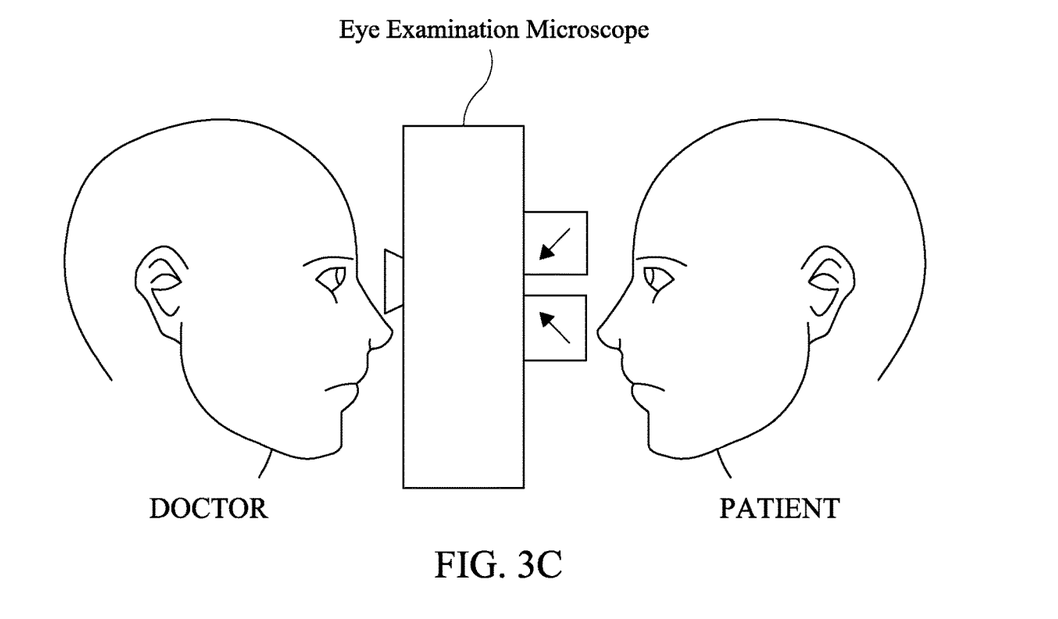
FIG. 3C illustrates another aspect of a method for aligning the device with a subject.
Figure 3D:
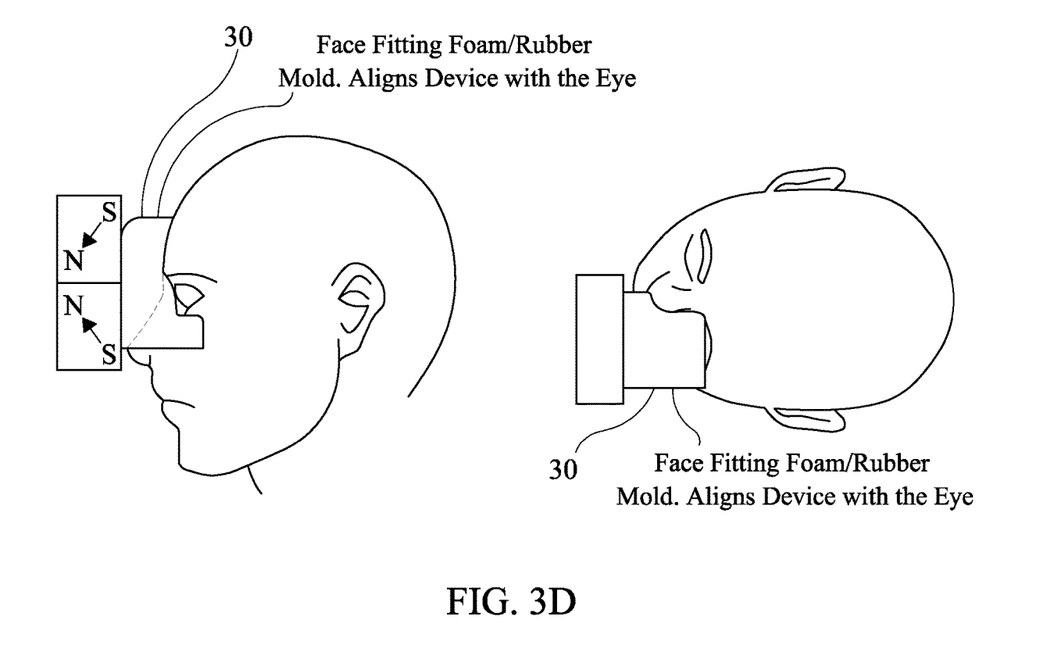
FIG. 3D illustrates another aspect of a method for aligning the device with a subject.

FIG. 2 illustrates a specific method, system and device to deliver active agents (drugs, genes, stem cells) into the eye. As shown in FIG. 1, the magnetic device 10 is capable of directing or applying a force 25 on magnetic, magnetically responsive, or magnetizable therapeutic agents 100 (e.g. magnetic nanoparticles coated with drugs), which can be used to direct such agents into the eye. As illustrated, the device 10 has magnets 12 or elements 12 magnetized capable of creating a node 30 (a magnetic field minimum) between the device 10 and the eye or parts of the eye. In an exemplary use, the magnetic therapeutic agents (e.g. nanoparticles coated with or containing a drug/therapy to be delivered to the vitreous humor or retina) would be placed in a gel on the surface of the eye or as a fluid contained within a carrier/holder 20, e.g., of a contact lens. The agent may be placed on the eye, in a liquid (e.g., saline), gel, or via other techniques. Then the magnetic device 10 can be placed in proximity to the eye aligned properly to create magnetic forces for targeting the agent to a specific region or to specific site within the eye. These forces would then magnetically direct some of the agents from the gel or fluid, through the sclera of the eye, into the vitreous humor and/or to the retina, thus delivering treatment to the interior of the eye.

In one example, a system includes (a) a carrier 25 that is a single-use reservoir (e.g., eye cup) containing therapy-conjugated magnetic nanoparticles (MNPs), and (b) a device 10 that is configured to push the MNPs through the sclera or cornea and into the retina. As can be seen, the magnetic device may then be held near the eye to apply magnetic forces on the agents. The magnetic forces then "push" or direct the agents through the eye to a desired location. This system can enable therapy delivery into the eye without or with reduced the need to puncture the eye with a syringe.

FIGS. 3A-3D illustrate a practicable method to deliver active agents into the eye using device 10. In this illustration, the device 10 can direct or apply force on a magnetic or magnetizable or magnetically-responsive therapeutic agents (e.g. magnetic nanoparticles coated with drugs) to direct such agents into the eye. The agents may be placed on the eye using conventional or future developed techniques, e.g., noninvasive or surgical techniques. The device 10 could be mounted on a standard eye examination microscope. A form fitting mold 30 (e.g. foam or rubber) could be attached to the device, such that when the mold is laid over the patients face, the device is at the proper location. One could have different molds for different patient head sizes (small, medium, and large). The magnetic device then can be aligned using a through hole, e.g. a viewing hole through which the practitioner lines up the device with the subject's eye. The device 10 may have a pivot, or other mechanism, so that the magnetic elements can be adjusted with respect to each other, to move the magnetic push node back and forth, e.g. for subjects with different sized heads, different sized eye sockets, or different sized eyes.

As can be seen, the magnetic device may then be held near the eye to apply magnetic forces 25 on the agents. The magnetic forces "push" or direct the agents through the eye membrane and into the eye sclera. In some examples, it is possible to deliver effective amounts of agents to the eye where previously delivery was not feasible. Or it is possible to deliver agents into the eye with a non-invasive procedure (no needles, no surgery) whereas previously an invasive procedure that included puncturing the eye.

Figure 4A:
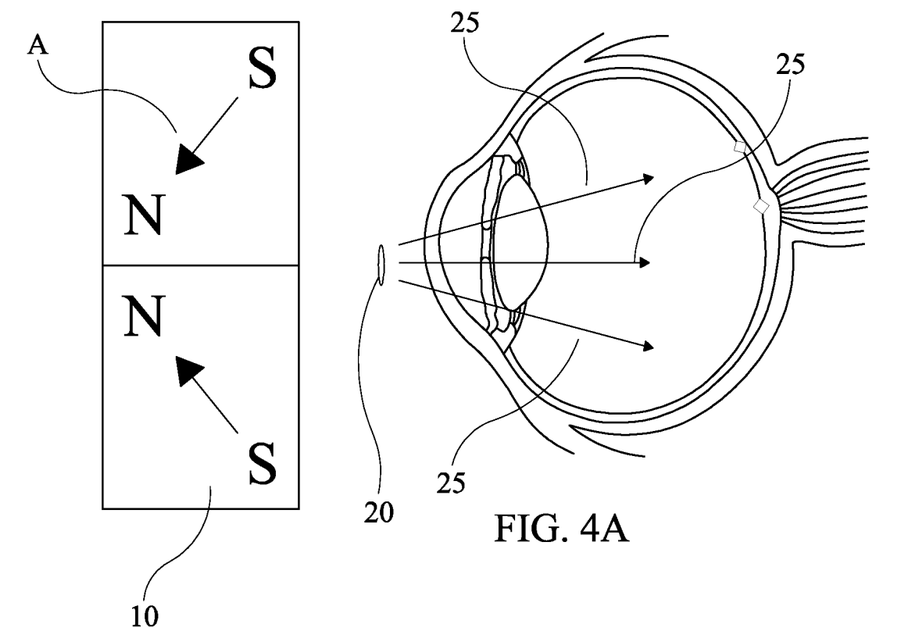
FIG. 4A shows one illustrative example of a device suitable with certain embodiments.
Figure 4B:
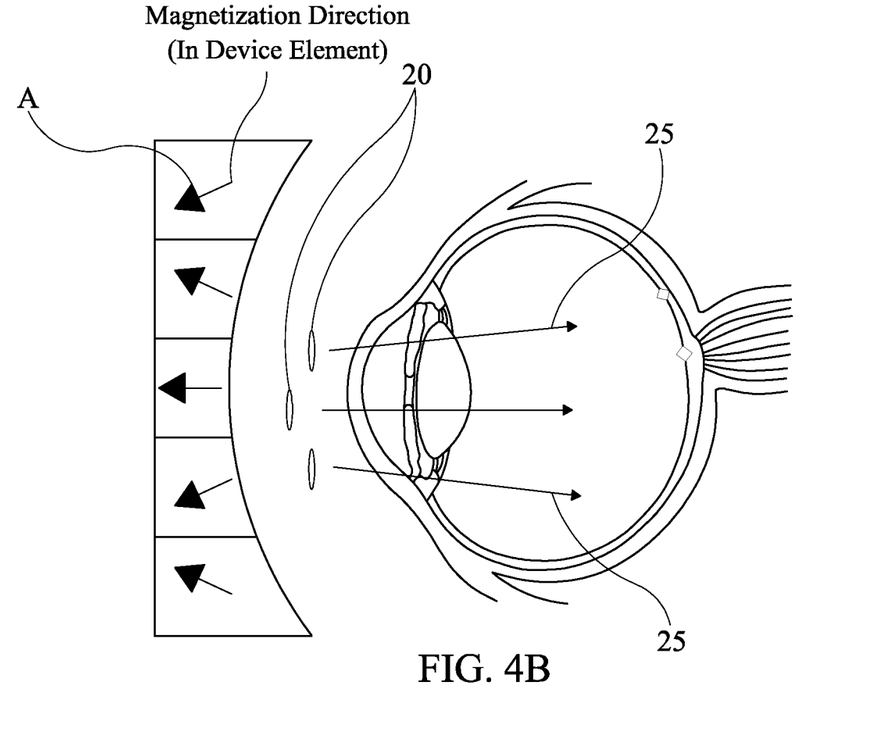
FIG. 4B shows one illustrative example of a device suitable with certain embodiments.
Figure 4C:
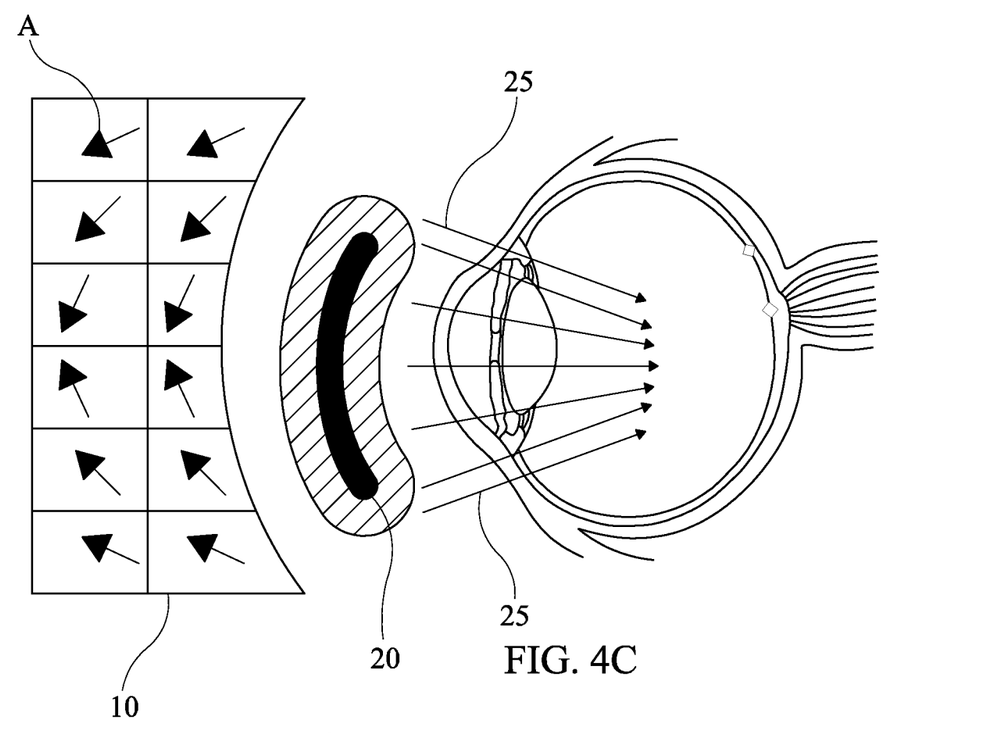
FIG. 4C shows one illustrative example of a device suitable with certain embodiments.

FIGS. 4A-4D show exemplary device implementations of varying complexity. FIG. 4A shows an example having elements magnetized to create a node (a magnetic field minimum). Magnetization of each element at an angle A is shown, here and throughout this disclosure, by the arrows from S (South) to N (North). Magnetization angles are chosen to place a push node 20 of zero or locally minimal magnetic field strength at a desired location. Forces on carriers go from low to high magnetic field strength. So forces on the carriers emanate out from this node, into the eye (for illustration, as a fan). FIG. 4B shows a device, with 5 exemplary elements magnetized at angles, creating 3 nodes. Each of the nodes has forces that go out from it. The forces are more focused into the eye (having no or less fanning out). The device can have more nodes based on preferences. FIGS. 4C show a "distributed node" device. The dark region is a region of zero or low magnetic field strength and forces point outwards from that region.

Figure 4D:
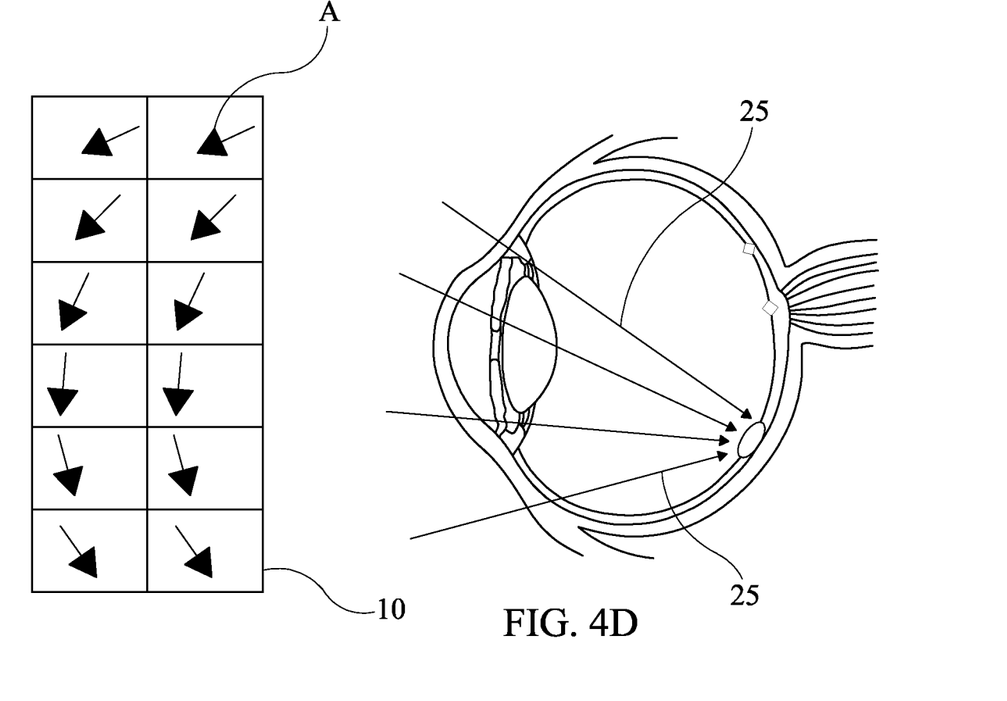
FIG. 4D shows one illustrative example of a device suitable with certain embodiments.

A device version that directs carriers to a target area on the eye, e.g. to a specific spot on or near the retina. FIG. 4D shows a device, having a focused magnetic push force field, capable of directing agents to a specific target into the eye, e.g. to a specific spot on the retina. As can be seen here, there are multiple focuses at multiple nodes and these forces are focused or can be focused to provide a push force field to a desired target. These four illustrative examples show that the magnetization directions of the elements can be controlled and varied using parameters selected using quadratic programming approach, or by other optimization methods. See, A. Sarwar, A. Nemirovski, B. Shapiro, "Optimal Halbach Permanent Magnet Designs for Maximally Pulling and Pushing Nanoparticles", *Journal of Magnetism and Magnetic Materials (JMMM)*, vol 324, issue 5, pg 742-754, March 2012, which is incorporated by reference.

In one specific embodiment the device for directing an agent into an eye has a plurality of magnetic elements that (a) produces a magnetic field at a node that applies a force on the agent, and (b) is structured to apply a magnetic force into the eye. The device can produce multiple nodes and can focus the force. The node is 0.001 cm to 3 cm from the device or 0.01 cm to 1.5 cm from the device.

In another specific embodiment, there can be a system for directing an agent into or through tissue (eye), comprising: an agent that is magnetic or magnetizable or magnetically responsive; and a magnetic configuration having a plurality of magnetic elements that (i) produces a first magnetic field at a local minimum that applies a force on the agent, and (ii) is structured to apply a magnetic force into the eye, and a holder configured to hold the agent proximal to the eye. The magnetization can create one or more nodes and magnetic push forces.

For illustration, selection and/or optimization of magnetization orientation for magnetic elements inside the device can be achieved by using physical principles to phrase the device design task as a constrained non-convex quadratic optimization technique. This quadratic optimization problem can be converted into an equivalent linear constrained optimization by a change of variables. Relaxing one constraint yields a new problem, now convex, whose solution is an upper bound for the original non-convex constrained quadratic problem, a method known as semidefinite relaxation (SDR). A lower bound is extracted from the upper bound matrix solution of the SDR problem by shrinking the solution matrix eigenvector with the maximum eigenvalue so that a new solution matrix does satisfy all the linear constraints. This yields a solution that satisfies the change-of-variable constraints but that is sub-optimal and therefore provides a rigorous lower bound. The lower bound can be then increased by optimizing a modified convex function that approximates the original non-convex quadratic problem. As the optimization proceeds, specific element magnetization directions are found each creating a specific but sub-optimal magnetic force. This method can converge to a final design that is squeezed between the lower and upper bounds and is to be the globally optimal solution. Thus this method can efficiently find a globally optimal (best possible) magnetic injector design for the eye. Further, a subsequent shape optimization that selects those elements that are maximally effective can further select optimal magnetization directions of the elements and an optimal shape for the magnetic injector. The above methods provide a mathematical framework to efficiently design the magnetic injector device (its shape, the magnetization angles for each of its elements) in order to achieve the desired magnetic forces (fan out, fan in, focused to a specific target, etc.).

As can be seen from FIGS. 4A-4D, one specific embodiment includes a method for delivering a therapeutic agent into the eye. More specifically, the active agent may be placed on the outer eye or within the eye and then be pushed or directed to a desired location within the eye.

Another embodiment includes a device for delivering magnetizable agents to a treatment site. An arrangement of magnets creates a magnetic field that results in push forces, and these forces can be used to push in (magnetically inject) magnetic or magnetizable or magnetically-responsive agents. More particularly, the device pushes outwards or magnetically injects magnetic or magnetizable or magnetically responsive carriers through tissue or materials. Specifically, it creates forces on magnetic, paramagnetic, ferrimagnetic, ferromagnetic, or superparamagnetic materials, and transports them outwards from the device (e.g., the magnetic injector). In specific examples, the device can be configured for application to eye treatments.

In another embodiment, the device shape and magnetization angles of its elements may be chosen so that the magnetization or magnetic forces are arranged to provide "push" or injection forces in an annular or "donut" region or a part thereof. This enables magnetic pushing of magnetic or magnetizable or magnetically-responsive carriers only through the sclera and iris portions of the eye, and would not apply push forces through the cornea, pupil, or lens of the eye. This structure can be useful in embodiment in which the practitioner is seeking to deliver the agents around the lens (rather than through the lens). For instance, such a magnetic injector design may be advantageous to improve safety by only directing carriers though the sclera and iris, and not directing carriers through the more critical cornea, pupil, and lens components of the eye.

Figure 5:
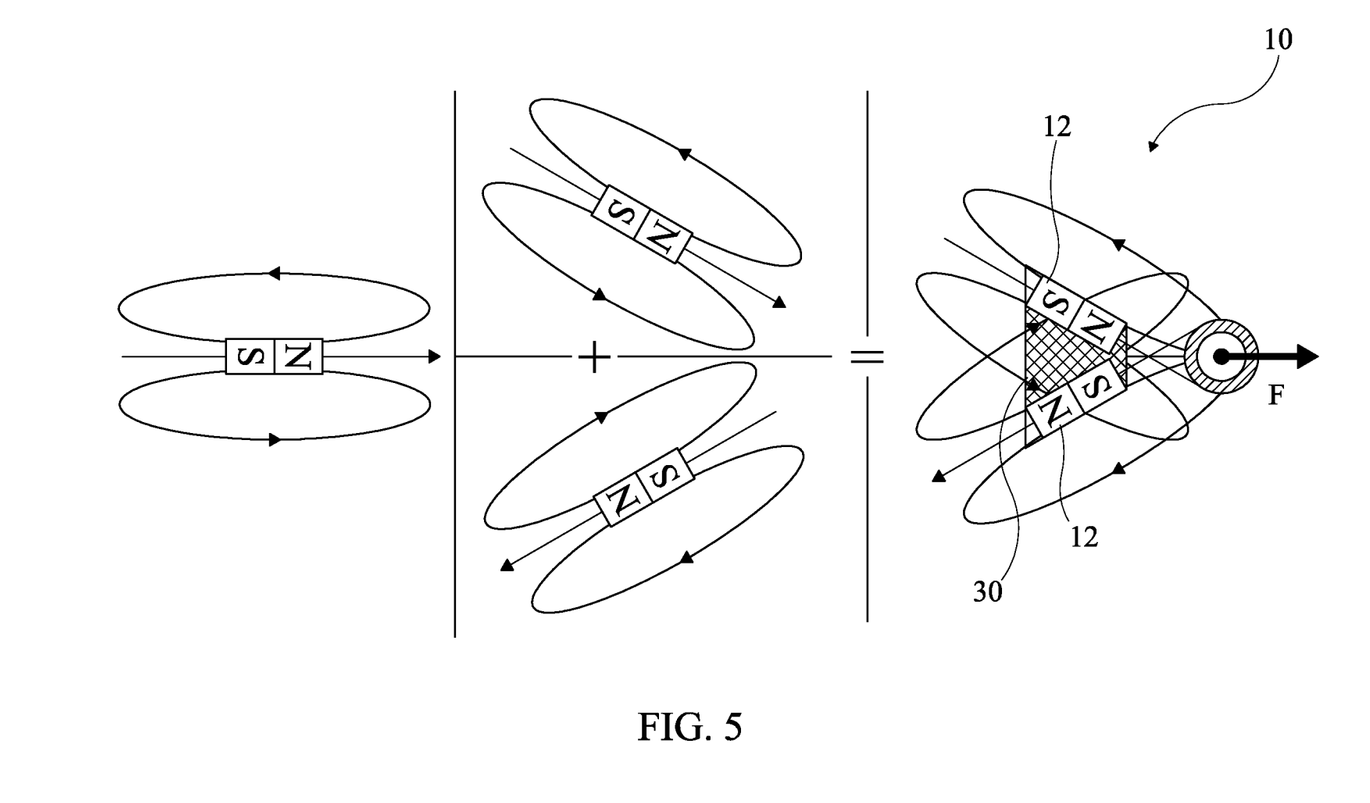
FIG. 5 showing the magnetic field and force relationship employed in certain specific embodiments.

One exemplary device suitable with this method includes a device that includes a housing and a plurality of magnetic elements or magnets that may be capable of generating magnetic fields. Typically, a single magnet can have field lines around it. The magnet can be set at an angle that creates a magnetic field along the horizontal x-axis at a desired location. A second magnet, with an opposite polarity, can be placed and angled in a configuration with respect to the first magnet so that the magnetic field is equal and opposite (along the minus x-axis) at the same desired location. See, e.g., FIG. 5. The cancellation of the two fields can then create a node—a magnetic field zero or minimum. In one example, these two magnets are arranged such that the two magnetic fields overlap and can cancel at the location of the desired node point without canceling around that point. In one embodiment, a local magnetic field minimum can be created with a higher magnetic field surrounding the node. This creates magnetic forces, from regions of low to high magnetic field strength—from the node out—and thus push the magnetic or magnetizable agents away from the magnetic injection device.

Alternatively, an exemplary device suitable with this method includes a device includes a housing and an electromagnet or combinations of electromagnets. The electromagnet may be capable of generating magnetic fields, which result in forces that can direct or push therapeutic agents. Such exemplary devices may have one or more permanent magnets or magnetic elements and/or one or more electromagnets.

A system for directing an agent into or through tissue having an agent that is magnetic, magnetizable or magnetically responsive; and a magnetic configuration having a plurality of magnetic elements that (i) produces a first magnetic field at a node that applies a force on the agent, and (ii) is structured to apply a magnetic force into the eye. The device has have multiple notes as illustrated herein; and the forces from the device may be focused to produce a suitable push force. The holder can be configured to hold the agents proximal to the eye.

The plurality of magnetic elements are disposed in the housing and the magnetic field can have the effect to displace the agent into the eye, at a rate determined in part by the strength of the magnetic field. The magnetic device 10 can push therapeutic agents into the eye.

In use and practice, active agents, i.e., magnetic or magnetizable or magnetically-responsive agents, can be for example magnetic nanoparticles coated with or containing drugs or other therapy, can be delivered from an initial location to another site (e.g., a treatment site). For example, such agents can be placed on the tissue or other surface as agents in a fluid (e.g. nanoparticles suspended in water), or agents in a gel, or as a powder, or as a paste, delivered in or via a flow, or by any other means that will reliably deliver them to a starting location. Then, the device is held in the vicinity of the magnetic or magnetizable agents, in such a way that the forces generated on the agents transport the agents from the starting to a desired location or treatment site. This magnetic injection force can transport the agents through a barrier. For example, the starting location could be, respectively, the surface of the eye or it could be near the surface of the eye or underneath the surface of the eye, and then the device can push the agent into the eye or through the eye, e.g. to a target within the eye.

In some examples, the device is placed between 0.01 and 3 cm from the eye. In other embodiments, the device is place between 3 cm and 10 cm from the eye. In yet other examples, the device is placed further from the eye.

The initial placement of the therapeutic agent can be accomplished in numerous ways. For example, such agents can be placed using the direct access to the eye in a liquid, a gel, by an atomizer (in a spray), or by other techniques. For another example, the agents may be placed on the eye using a syringe, contact lens, eye drops, or another material that is impregnated with agents and can be placed on the eye. In one example, the agent or therapeutic agent can be placed mechanically (e.g., by injection) in the eye and the magnetic push force can push the agent in the eye. In certain embodiments, the agents may permeate into the eye.

Once the formulation has been placed onto or into the eye, the patient is exposed to a magnetic field in order to cause the agents to migrate, for example, through the sclera, iris, and vitreous cavity to the desired position within the eye, for example to the macula on the retina.

The strength of the magnetic field to be employed may vary from application to application but will generally be in the range of from about 0.001 to about 10 Tesla. In another embodiment, the magnetic field will employ a strength between 0.5 to 5 Telsa. In another embodiment, the magnetic field will employ a strength between 0.2 to 2 Tesla.

In some embodiments, the carriers or attached therapeutic agents may be visible in the unaided eye in order to enable in visual tracking of the applied therapy. Such carriers/agents may be visible to an unaided eye (e.g., of a practitioner) or an eye aided by a microscope. A practitioner may adjust the magnetic injector device to direct agents and therapy to the desired target if he or she observes that the agents/therapy are not yet at the desired location.

In another embodiment, readily visible materials can be bound to therapeutic agents together with magnetic particles so as to provide visual labels in the eye. Such labels may be associated with the magnetic particles in order to aid in visual tracking of the therapeutic agent. Such particles may be visible to an unaided eye or an eye aided by a microscope.

In yet other embodiments, fluorescent or photoluminescent materials such as luminescent chromophores or dyes may be bound to the therapeutic agents, or to magnetic particles together with therapeutic agents, or on particles separate from the therapeutic agent. Such labels may be associated with the magnetic particles in order to aid in visual tracking of the therapeutic agent.

The formulations of the pharmaceutical compounds that can be administered in connection with the methods comprise therapeutic agents, pharmaceutical agents (such as steroids, anti-inflammatory, or oto-protectant agents), molecular agents, nucleotides, proteins, or cells (e.g. stem cells) loaded with magnetizable particles.

The magnetic agents can be or can include therapeutics, drugs, proteins, or gene therapy, either by having these materials themselves be magnetic (e.g. a drug molecule that is magnetic), by incorporating magnetic materials either on a molecular basis (e.g. drug molecules that include iron) or by being bound or attached to magnetic materials. Magnetic agents that are made by placing magnetic materials inside or attaching them to non-magnetic objects (e.g. to starch or polymer objects, to/in micelles, liposomes, viruses, bacteria, cells) can themselves be therapeutic or can further contain therapeutics, drugs, proteins, or gene therapy on their surfaces or inside them. Non-magnetic agents (such as therapeutics, drugs, proteins, or gene therapy) can also be magnetically pushed by attaching them to or containing them inside agents that are or have been made magnetic. Binding, encapsulation, coatings, and other means may be chosen to most advantageously select the therapy release rates (slow or fast), release times (immediately or after a certain duration), and conditions under which release will occur (pH, osmolarity, or other parameters) to most efficaciously treat target regions or locations. The agents may be formulated into powders, suspensions, gels, sprays, lotions, or other formulations known in drug delivery.

Therapeutics and drugs can include steroids (e.g. dexamethasone, prednisone, methylprednisolone, betamethasone), prostoglandins, anti-inflammatory agents, aminoglycosides, antibiotics (e.g. glycosides), drugs meant to retard the growth of blood vessels (e.g. anti-VEGF monoclonal antibody fragments, Lucentis), or other drugs, and nucleotide or gene therapy. They can include target-specific ligands, linkers to other moieties, polar or non-polar moieties, and elements that can be used to help transport agents across physiological barriers.

Such pharmaceutical compositions can contain a therapeutically effective amount of active ingredients, and, as may be necessary, inorganic or organic, solid or liquid pharmaceutically acceptable carriers. Pharmaceutical compositions suited for topical/local administration to the eye include aqueous solutions or suspensions, which may either be ready to use or require preparation prior to use (e.g. lyophilisates). Suited pharmaceutical compositions further include gels, which may be biodegradable or non-biodegradable, aqueous or non-aqueous, or micro- or nano-sphere based. Examples of such a gel include, but are not limited to, carbomers, poloxamers, alginates, hyaluronates, xyloglucans, polyesters, polysaccharides, poly(lactides), poly(glycolide) or their co-polymers PLGA, sucrose acetate isobutyrate, and glycerol monooleate, whereas the gel may be formed in situ or prior to use from solutions or suspensions. These compounds further include creams and ointments, emulsions, micro-emulsions or self-emulsifying compositions. Pharmaceutical compositions suited for enteral or parenteral administration include tablets or gelatine capsules or aqueous solutions or suspensions as described above.

The pharmaceutical compositions may be sterilized and/or may contain adjuvants, e.g. preservatives, stabilizers, wetting agents and/or emulsifiers, salts for regulating the osmotic pressure and/or buffers, penetration enhancers, bioadhesive agents. The pharmaceutical compositions of the invention may, if desired, contain further pharmacologically active substances, such as, but not limited to antibiotics or analgesics. They may be prepared by any of the methods, e.g. by conventional mixing, granulating, confectioning, dissolving or lyophilizing methods, and contain from about 0.01 to 100% of active ingredient.

The amount to be administered may vary, depending upon the method of administration, duration of therapy, the condition of the subject to be treated, and the severity of the eye disease. The duration of therapy injection may range between one minute and several hours for a single treatment, and could be administered once or multiple times over a period of days, weeks, months, or years, and may extend up to chronic treatment. The therapeutically effective amount of the compound to be delivered may range between picograms to milligrams.

The agent should be magnetic or magnetizable or magnetically-responsive (that is associated with magnetic or magnetizable materials). Alternatively, the agent can be applied topically and then delivered to the targeted site. Suitable modalities are available to deliver agents to a site away from or proximal to the target site.

Magnetic materials can include paramagnetic, ferrimagnetic, ferromagnetic and superparamagnetic materials (e.g. iron containing compounds), martensitic stainless steels (e.g. 400 series), iron oxides ($Fe_2O_3$, $Fe_3O_4$), neodymium iron boron, alnico (AlNiCo), and samarium cobalt ($SmCo_5$). Moreover, individual magnetic materials have been shown to possess properties that can be combined to achieve localized delivery. Ferromagnetic and superparamagnetic compounds include but are not limited to iron-containing compounds such as martensitic stainless steels (e.g. 400 series), iron and iron oxides ($Fe_2O_3$, $Fe_3O_4$).

If the agent is diamagnetic or if the magnetic material associated with the agent is diamagnetic, then the combined force from the device or system can attract the agent or associated diamagnetic material. Diamagnetic materials, all paired electrons, are slightly repelled by a magnetic field. Diamagnetic properties arise from the realignment of the electron orbits under the influence of an external magnetic field. The use of diamagnetic materials may reverse the interactions with the device or system.

In one exemplary embodiment, the magnetic material is in the form of micron-sized or sub-micron-sized particles. Such particles may be incorporated in micro or nano-carriers, optionally the micro or nano-carriers contain an active agent to be delivered. Suitable sizes for the magnetic material range from nanometers up to centimeters in cross-sectional diameter or width. In another exemplary embodiment, the magnetic material is larger than 1 nanometers in length, width, and/or diameter, and may have any shape (e.g. tubes, ellipses, etc.).

Magnetic particles may be incorporated into cells or attached to cell surfaces by procedures known to those skilled in the art. In certain exemplary embodiments, magnetic particles may be fed to the target cells or temporary pores may be created in the cell membrane of the target cell by electroporation. In other exemplary embodiments, magnetic particles may be attached to the cell surface via an antibody binding to cell membrane receptors or through chemical conjugation of the magnetic particle to the cell membrane.

One or more agents may be formulated alone or with excipients or encapsulated on, in or incorporated into the microparticles or nanoparticles. Suitable agents include therapeutic, prophylactic, and diagnostic agents. These agents include organic or inorganic compounds, amino acids and proteins, sugars and polysaccharides, nucleic acids or other materials that can be incorporated using standard techniques.

In some exemplary embodiments, the agents may be biocompatible. Such agents may further be eliminated by natural processes from the eye, by metabolism, by mucosal uptake and delivery to the blood, and by other physiological means and may eventually be cleared from the eye. Nevertheless, if after the magnetically injected therapy has acted in the eye (for example, after drugs have been released from the agents into the eye), if it is desirable to remove the agents from the eye, a magnet could be held near that eye. In reverse to the magnetic injection device, which applied injection forces, this magnet would pull the agents back out.

The term "therapeutically effective" refers to an amount of composition that is sufficient to ameliorate one or more causes or symptoms of a disease or disorder. Such amelioration only requires a reduction or alteration, not necessarily elimination of the disease or disorder. A therapeutically effective dose includes an amount effective to produce a desired effect, such as restoration of sight, improvement to sight, and reduction in loss of sight, and treatment of eye conditions.

Treatments of device 10 may be given to a subject only once, or repeatedly at required intervals. For example, steroids are typically administered about every three months. Further, this treatment may be carried out in conjunction with other treatment protocols, such as systemic drug treatments (e.g. antibiotics) or various surgical procedures, as warranted for a specific situation.

The agent sizes, shapes, and coatings can be varied and selected based on application parameters. The magnetic force on an agent typically varies with the volume of magnetic or magnetizable materials in that agent. Thus, to increase magnetic forces, it is desirable to choose larger agents. Larger agents may also create more damage to tissue as they move through it. For this reason, there is an anticipated tradeoff: it is suitable to pick agents that are big enough to experience sufficient magnetic forces but small enough to move through tissue barriers easily and without causing undesirable damage. It is also desirable to choose agents with coatings or surfaces that allow easier passage through tissue barriers.

The magnetic forces created on agents by applied magnetic fields are known to a degree. For example, it is known that the magnetic force typically scales with the volume of magnetic or magnetizable material in the agent. Forces on agents can also be measured. Thus agents can be selected to provide a desired degree of magnetic forces.

Tissue forces on agents, the forces that resist motion through tissue barriers, are less well understood. Thus we disclose carrying out tissue and animal experiments to measure tissue/barrier resistance to agent motion as a function of agent size, shape, and coating. A sample experiment is to take agents of various sizes and measure their motion through a tissue sample of specified thickness under a carefully applied magnetic field for a variety of agent shapes, sizes, and coatings. The data from such measurements can be used to determine tissue resistance to agent motion for various agent sizes, shapes, and coatings. A measurement of the motion of the agent through tissue may be used to assist in optimization. In contrast, magnetic forces on agents can be accurately predicted in many cases, but if/when they cannot, then experiments can be used instead.)

Once magnetic forces and tissue/barrier resistance have been determined, either by calculations and/or via experimental measurements, then optimal agent size, shape, and coatings are chosen to provide the optimal tradeoff between magnetic forces and tissue/barrier resistance. For directing spherical ferromagnetic nanoparticles into the eye over adult human distance (0.001-6 mm from magnetic injection device to agents placed in the eye), an effective sample size of nano-particles with iron cores is approximately 100 nm in diameter. However, it is evident that magnetic particles as small as 20 nm and as large as 1 micrometer can be pushed.

Methods and devices disclosed herein may be used with animals and humans. The term "subject," and "patient" are used interchangeably to refer to any individual who is the target of administration or treatment. The subject can be a vertebrate, for example, a mammal. Thus, the subject can be a human or veterinary patient.

EXAMPLES

The disclosure will be further described in connection with the following examples, which are set forth for purposes of illustration only.

Exemplary 1

Magnetically Directing Therapeutic Agents into the Eye

The magnetic device can be used to deliver therapeutic magnetic or magnetizable agents into the eye of animals and humans. The magnetic or magnetizable agents were placed on the eye. The magnetic device was then held so that magnetic forces on the agents act to transport or push them into the eye.

The particles can be functionalized with heparin and adeno-associated viral vectors for treatment of Leber's congenital amaurosis. Particles can also be functionalized with other drugs, for example anti-VEGF monoclonal antibody fragments, Lucentis for treatment of macular degeneration.

Figure 6A:
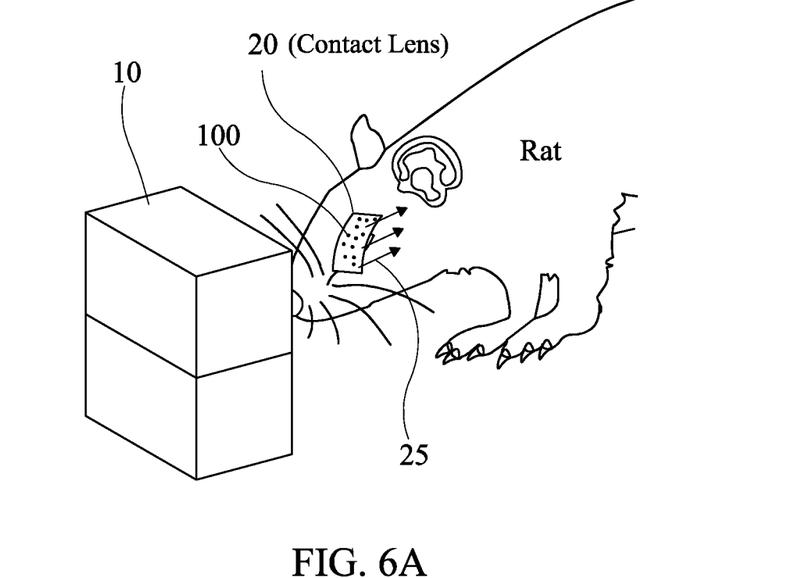
FIG. 6A illustrates aspects of an animal experiment.
Figure 6B:
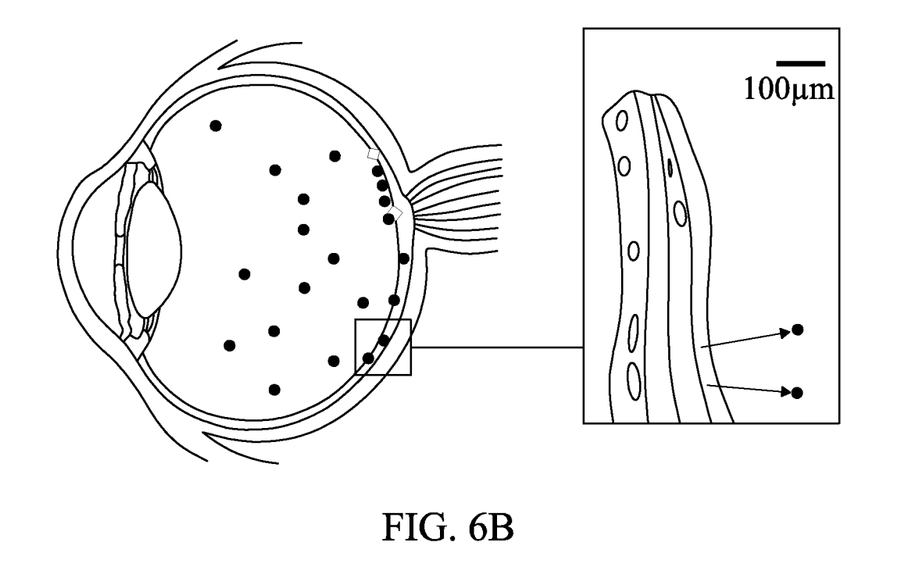
FIG. 6B illustrates schematic certain aspects of an animal experiment.

In rat experiments and as shown in FIGS. 6A and 6B, a 1 cm size contact lens with forty microliters of 100 nm diameter starch coated magnetic nano-particles within the well of the contact lens was placed on the eye, and the magnetic push system was aligned to push the magnetic particles to the retina for one hour, at which point the animal was sacrificed and its eye excised. The presence of nano-particles in the eye was verified by histology (with Perls' Prussian blue stain). The 3-dimensional distribution of the particles was measured by an automated 3D fluorescent imaging cryostat system.

The delivery system creates a magnetic cancellation node or nodes that pushes particles away from the magnets. The strong magnetic injection force provided by the delivery system (e.g. picoNewtons/particle) allow for the creation of a non-invasive (needle-free) system for clinicians to deliver particles with attached therapy into the eye.

Example 2

Device with Two Domains

FIG. 4A shows a schematic diagram of a device of single magnet with at least two domains (two sub-magnets) magnetized in two different directions. This magnet was placed in a device and optimized to magnetically inject agents into the eye.

Example 3

Animal Experiments

Animal experiments that were conducted to test and validated device described in Example 1. The device was made by bonding two magnets together, with each magnet magnetized as shown by the "S→N" (South to North) markings

The invention claimed is:

1. A method for treating an eye disease in a subject by pushing a therapeutic agent to a target location of a treatment site, the method comprising:
   (a) providing, by a delivery device, a plurality of push nodes each generated by overlapping combined magnetic fields of a plurality of magnetic elements, wherein each of the plurality of push nodes are local magnetic field strength minimums configured to emit magnetic forces, and wherein the magnetic elements are permanent magnets;
   (b) placing, the therapeutic agent locally on an eye of the subject;
   (c) aligning, the delivery device, to configure the plurality of push nodes to emit magnetic forces directionally towards the target location; and
   (d) pushing, by the plurality of push nodes, the therapeutic agent, wherein a predetermined amount of the therapeutic agent is pushed into the eye by the magnetic fields to the target location of the treatment site;
   wherein at least two magnetic elements of the plurality of magnetic elements of the delivery device are pivotably arranged at an angle with respect to each other via a pivot mechanism in the delivery device; and
   wherein the therapeutic agent permeates into the eye, and the magnetic forces emanating from a first push node of the plurality of push nodes and a second push node of the plurality of push nodes push the therapeutic agent to a first target location and a second target location within the interior of the eye.

2. The method as claimed in claim 1, wherein the therapeutic agent is magnetic, superparamagnetic, ferromagnetic, ferrimagnetic, or paramagnetic.

3. The method as claimed in claim 1, wherein the therapeutic agent is a carrier and the carrier is biodegradable.

4. The method as claimed in claim 1, wherein the therapeutic agent is magnetic, magnetizable, and magnetically responsive.

5. The method as claimed in claim 1, wherein magnetization of each of the at least two magnetic elements of the plurality of magnetic elements of the delivery device are arranged at the angle with respect to each other.

6. The method as claimed in claim 1, wherein the therapeutic agent is placed on the eye of the subject, without puncturing the exterior of the eye with a syringe.

7. A method to decrease eye trauma in a subject while treating an eye disease in an eye of the subject, the method comprising:
   (a) generating, by a delivery device, a magnetic field using a plurality of magnetic elements, wherein:
      the plurality of magnetic elements are permanent magnets, and wherein the plurality of magnetic elements includes a first set of magnetic elements having a first magnetization and a second magnetization, and produces a first magnetic field and a second magnetic field, the first magnetic field and the second magnetic field overlap to create a first combined field and a first push node that is configured to emit a first set of magnetic forces; and
      the plurality of magnetic elements includes a second set of magnetic elements having a third magnetization and a fourth magnetization, and produces a third magnetic field and a fourth magnetic field, the third magnetic field and the fourth magnetic field overlap to create a second combined field and a second push node that is configured to emit a second set of magnetic forces;
   (b) placing, a therapeutic agent locally on the eye of the subject;
   (c) placing, the delivery device, proximal to the subject;
   (d) pushing, by the first and second push nodes, the therapeutic agent using the first set and second set of magnetic forces, wherein the exterior of the eye is materially intact during a treatment; and
   (e) adjusting, the plurality of magnetic elements with respect to each other via a pivot mechanism in the delivery device to configure the first set of magnetic forces to aligned directionally towards a first target location and the second set of magnetic forces to aligned directionally towards a second target location;
   wherein at least two magnetic elements of the plurality of magnetic elements of the delivery device are pivotably arranged at an angle with respect to each other; and
   wherein the therapeutic agent permeates into the eye, and the magnetic forces emanating from the first push node and the second push node push the therapeutic agent to the first target location and the second target location within the interior of the eye.

8. The method as claimed in claim 7, wherein the therapeutic agent is placed on the exterior of the eye, and the exterior of the eye is sclera, cornea, iris, pupil, or lens.

9. The method as claimed in claim 8, wherein the therapeutic agent is placed on the exterior of the eye, without puncturing the exterior of the eye with a syringe.

10. The method as claimed in claim 7, wherein the therapeutic agent is placed mechanically onto the eye and the delivery device pushes the therapeutic agent to first target location and second target location within the eye.

* * * * *